United States Patent
Vissa et al.

(10) Patent No.: US 10,166,438 B2
(45) Date of Patent: Jan. 1, 2019

(54) APPARATUS, METHOD, AND PROGRAM PRODUCT FOR TRACKING PHYSICAL ACTIVITY

(71) Applicant: Motorola Mobility LLC, Chicago, IL (US)

(72) Inventors: Sudhir Vissa, Bensenville, IL (US); Douglas Lautner, Round Lake, IL (US); Vivek Tyagi, Chicago, IL (US)

(73) Assignee: MOTOROLA MOBILITY LLC, Chicago, IL (US)

( * ) Notice: Subject to any disclaimer, the term of this patent is extended or adjusted under 35 U.S.C. 154(b) by 0 days.

(21) Appl. No.: 15/484,465

(22) Filed: Apr. 11, 2017

(65) Prior Publication Data

US 2018/0290020 A1     Oct. 11, 2018

(51) Int. Cl.
*A63B 24/00* (2006.01)
*H04W 8/00* (2009.01)
*H04L 29/08* (2006.01)

(52) U.S. Cl.
CPC ......... *A63B 24/0062* (2013.01); *H04W 8/005* (2013.01); *H04L 67/306* (2013.01)

(58) Field of Classification Search
CPC ... A63B 24/0062; A63B 24/00; H04W 8/005; H04W 8/18; H04L 67/306; H04L 67/22; H04L 67/18; H04L 67/24; H04L 51/00; H04L 51/046; H04L 51/32; H04L 63/10; H04L 63/104; H04L 63/0861; H04L 63/102; G06F 3/16; G06F 3/167; G06F 21/32; G06F 21/50; G06F 1/1613; G06F 1/163; G01C 22/00; G01C 22/006; H04M 2201/40; H04M 2250/74
See application file for complete search history.

(56) References Cited

U.S. PATENT DOCUMENTS

| | | | |
|---|---|---|---|
| 8,001,179 B2* | 8/2011 | Jung | G06N 5/04 709/203 |
| 8,478,251 B1* | 7/2013 | Okolo | G06Q 10/10 455/414.1 |
| 8,788,621 B2* | 7/2014 | Okamoto | H04L 67/22 709/218 |

(Continued)

OTHER PUBLICATIONS

Kellee Bryan, "8 Fitness Apps That Use Your Friends (for motivation) (blog/8-fitness-apps-that-use-your-friends)", EveryMove blog, Dec. 21, 2012, 6 pages.

(Continued)

*Primary Examiner* — Brian Wilson
(74) *Attorney, Agent, or Firm* — Kunzler, PC (57) ABSTRACT

Apparatuses, methods, and program products are disclosed for tracking physical activity. One apparatus includes a processor, and a memory that stores code executable by the processor. The code is executable by the processor to detect, by use of the apparatus held by a first person, a second person in close proximity to the first person. The code is executable by the processor to track physical activity of the first person. The code is executable by the processor to transmit at least a portion of the tracked physical activity of the first person to an electronic identity corresponding to the second person to enable attaching at least the portion of the tracked physical activity of the first person to the electronic identity corresponding to the second person.

15 Claims, 7 Drawing Sheets

(56) References Cited

U.S. PATENT DOCUMENTS

| | | | | |
|---|---|---|---|---|
| 8,918,903 | B1* | 12/2014 | Schepis | G06F 21/316 709/224 |
| 9,288,298 | B2* | 3/2016 | Choudhary | H04L 51/00 |
| 9,344,546 | B2* | 5/2016 | Choudhary | H04L 51/00 |
| 9,565,179 | B2* | 2/2017 | Zou | H04L 63/0815 |
| 9,712,629 | B2* | 7/2017 | Molettiere | H04L 67/22 |
| 9,734,477 | B2* | 8/2017 | Weast | G06F 19/00 |
| 2006/0007315 | A1* | 1/2006 | Singh | H04N 1/32128 348/207.99 |
| 2013/0138716 | A1* | 5/2013 | Macwan | G06Q 30/02 709/203 |
| 2013/0176142 | A1* | 7/2013 | Drysdale | G06F 3/011 340/870.02 |
| 2014/0099614 | A1* | 4/2014 | Hu | G09B 19/00 434/236 |
| 2014/0244429 | A1* | 8/2014 | Clayton | G06Q 30/0631 705/26.7 |
| 2014/0371887 | A1* | 12/2014 | Hoffman | G06K 9/00342 700/91 |
| 2016/0058336 | A1* | 3/2016 | Blahnik | A61B 5/1112 600/595 |
| 2016/0089569 | A1* | 3/2016 | Blahnik | G06Q 10/0639 434/247 |
| 2016/0343235 | A1* | 11/2016 | Belvin | G08B 21/24 |
| 2017/0061955 | A1* | 3/2017 | Gueta | G10L 13/04 |
| 2017/0309196 | A1* | 10/2017 | Vangala | G09B 19/00 |

OTHER PUBLICATIONS

Jeff Cattel et al. "The 39 Best Health and Fitness Apps of 2016", http://greatist.com/fitness/best-health-fitness-apps, Apr. 19, 2016, 11 pages.

Briallyn Smith, The Best Social Media Apps for Working Out with Friends, MUD social media, http://www.makeuseof.com/tag/the-best-social-media-apps-for-working-out-with-friends/, May 1, 2015, 15 pages.

Endo Eva, "Friends", Endomondo, https://support.endomondo.com/hc/en-us/articles/201784386-Friends, Nov. 2016, 12 pages.

* cited by examiner

APPARATUS, METHOD, AND PROGRAM PRODUCT FOR TRACKING PHYSICAL ACTIVITY

FIELD

The subject matter disclosed herein relates to physical activity and more particularly relates to tracking physical activity.

BACKGROUND

Description of the Related Art

Information handling devices, such as desktop computers, laptop computers, tablet computers, smart phones, optical head-mounted display units, smart watches, televisions, streaming devices, etc., are ubiquitous in society. These information handling devices may be used for performing various actions. Performing various actions, such as tracking physical activity, may be difficult to perform for people not having a device to track physical activity.

BRIEF SUMMARY

An apparatus for tracking physical activity is disclosed. A method and computer program product also perform the functions of the apparatus. In one embodiment, the apparatus includes a processor, and a memory that stores code executable by the processor. The code, in various embodiments, is executable by the processor to detect, by use of the apparatus held by a first person, a second person in close proximity to the first person. The code, in some embodiments, is executable by the processor to track physical activity of the first person. The code, in certain embodiments, is executable by the processor to transmit at least a portion of the tracked physical activity of the first person to an electronic identity corresponding to the second person to enable attaching at least the portion of the tracked physical activity of the first person to the electronic identity corresponding to the second person.

In some embodiments, the code executable by the processor performs detecting the second person in close proximity to the first person by detecting a wireless device corresponding to the second person. In one embodiment, the code executable by the processor performs detecting the second person in close proximity to the first person by detecting a voice profile corresponding to the second person.

In another embodiment, the code executable by the processor performs detecting the voice profile corresponding to the second person by comparing the voice profile to multiple voice profiles that are captured by the apparatus. In some embodiments, the code executable by the processor performs capturing the multiple voice profiles by controlling the apparatus to actively listen to phone conversations and associating a detected voice with a contact in a contact list.

A method for tracking physical activity, in one embodiment, includes detecting, by use of a first apparatus held by a first person, a second person in close proximity to the first person. In a further embodiment, the method includes tracking physical activity of the first person. In certain embodiments, the method includes transmitting at least a portion of the tracked physical activity of the first person to an electronic identity corresponding to the second person to enable attaching at least the portion of the tracked physical activity of the first person to the electronic identity corresponding to the second person.

In some embodiments, detecting the second person in close proximity to the first person includes detecting a wireless device corresponding to the second person. In various embodiments, detecting the second person in close proximity to the first person includes detecting a voice profile corresponding to the second person. In one embodiment, detecting the voice profile corresponding to the second person further includes: capturing audio input, comparing the audio input to multiple voice profiles, and selecting the voice profile of the multiple voice profiles that matches the audio input.

In some embodiments, detecting the second person in close proximity to the first person includes detecting an input to the first apparatus indicating that the second person is in close proximity to the first person. In certain embodiments, the method includes storing information corresponding to time periods during the tracked physical activity in which the second person is detected to be in close proximity to the first person. In various embodiments, tracking the physical activity of the first person includes tracking the physical activity of the first person using the first apparatus, a second apparatus, or some combination thereof. In one embodiment, detecting the second person in close proximity to the first person includes detecting the second person in response to beginning tracking the physical activity of the first person. In certain embodiments, the method includes obtaining the electronic identity corresponding to the second person in response to detecting the second person.

In one embodiment, a program product includes a computer readable storage medium that stores code executable by a processor. The executable code, in certain embodiments, includes code to perform detecting, by use of a first apparatus held by a first person, a second person in close proximity to the first person. The executable code, in some embodiments, includes code to perform tracking physical activity of the first person. The executable code, in various embodiments, includes code to perform transmitting at least a portion of the tracked physical activity of the first person to an electronic identity corresponding to the second person to enable attaching at least the portion of the tracked physical activity of the first person to the electronic identity corresponding to the second person.

In certain embodiments, the executable code includes code to perform storing information corresponding to time periods during the tracked physical activity in which the second person is detected to be in close proximity to the first person. In some embodiments, tracking the physical activity of the first person includes tracking the physical activity of the first person using the first apparatus, a second apparatus, or some combination thereof. In various embodiments, the executable code includes code to perform obtaining the electronic identity corresponding to the second person in response to detecting the second person.

In one embodiment, the executable code includes code to perform detecting a voice profile corresponding to the second person. In certain embodiments, the executable code includes code to perform detecting the voice profile corresponding to the second person further includes code to perform: capturing audio input, comparing the audio input to multiple voice profiles, and selecting the voice profile of the multiple voice profiles that matches the audio input.

BRIEF DESCRIPTION OF THE DRAWINGS

A more particular description of the embodiments briefly described above will be rendered by reference to specific embodiments that are illustrated in the appended drawings.

Understanding that these drawings depict only some embodiments and are not therefore to be considered to be limiting of scope, the embodiments will be described and explained with additional specificity and detail through the use of the accompanying drawings, in which.

DETAILED DESCRIPTION

As will be appreciated by one skilled in the art, aspects of the embodiments may be embodied as a system, apparatus, method, or program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain embodiment, the storage devices only employ signals for accessing code.

Certain of the functional units described in this specification have been labeled as modules, in order to more particularly emphasize their implementation independence. For example, a module may be implemented as a hardware circuit comprising custom very-large-scale integration ("VLSI") circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in code and/or software for execution by various types of processors. An identified module of code may, for instance, include one or more physical or logical blocks of executable code which may, for instance, be organized as an object, procedure, or function. Nevertheless, the executables of an identified module need not be physically located together, but may include disparate instructions stored in different locations which, when joined logically together, include the module and achieve the stated purpose for the module.

Indeed, a module of code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different computer readable storage devices. Where a module or portions of a module are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory ("RAM"), a read-only memory ("ROM"), an erasable programmable read-only memory ("EPROM" or Flash memory), a portable compact disc read-only memory ("CD-ROM"), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages including an object oriented programming language such as Python, Ruby, Java, Smalltalk, C++, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. These code may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus or other devices to produce a computer implemented process such that the code which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and program products according to various embodiments. In this regard, each block in the schematic flowchart diagrams and/or schematic block diagrams may represent a module, segment, or portion of code, which includes one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

Figure 1:
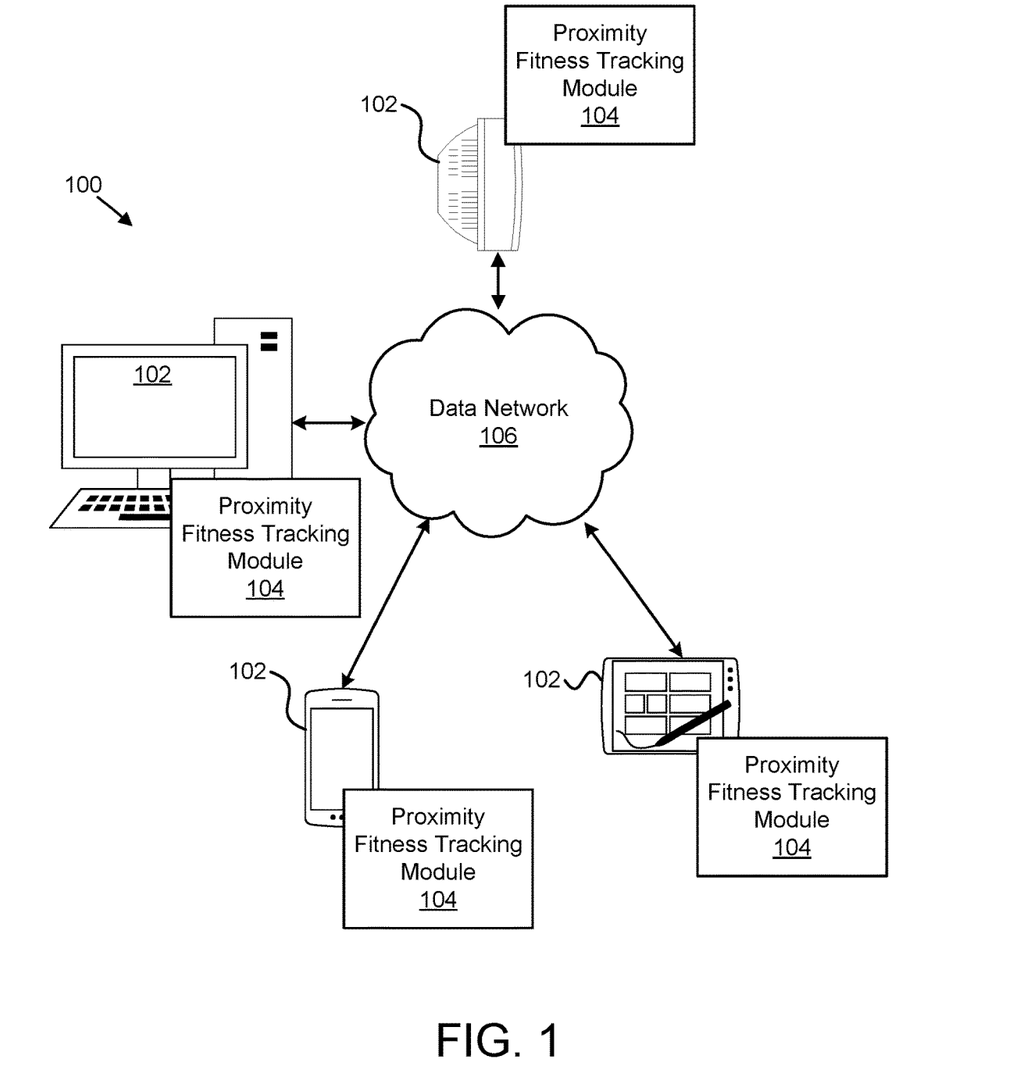
FIG. 1 is a schematic block diagram illustrating one embodiment of a system for tracking physical activity.

FIG. 1 depicts one embodiment of a system 100 for tracking physical activity. In one embodiment, the system 100 includes information handling devices 102, proximity fitness tracking modules 104, and data networks 106. Even though a specific number of information handling devices 102, proximity fitness tracking modules 104, and data networks 106 are depicted in FIG. 1, one of skill in the art will recognize that any number of information handling devices 102, proximity fitness tracking modules 104, and data networks 106 may be included in the system 100.

In one embodiment, the information handling devices 102 include computing devices, such as desktop computers, laptop computers, personal digital assistants (PDAs), tablet computers, smart phones, smart televisions (e.g., televisions connected to the Internet), set-top boxes, game consoles, security systems (including security cameras), vehicle on-board computers, network devices (e.g., routers, switches, modems), streaming devices, activity tracking devices, fitness tracking devices, or the like. In some embodiments, the information handling devices 102 include wearable devices, such as smart watches, fitness bands, optical head-mounted displays, or the like. The information handling devices 102 may access the data network 106 directly using a network connection.

The information handling devices 102 may include an embodiment of the proximity fitness tracking module 104. In certain embodiments, the proximity fitness tracking module 104 may detect, by use of a first apparatus held by a first person, a second person in close proximity (e.g., within 5-10 feet, within 5-15 feet, within 0-20 feet, etc.) to the first person. The proximity fitness tracking module 104 may also perform tracking physical activity of the first person. The proximity fitness tracking module 104 may perform transmitting at least a portion of the tracked physical activity of the first person to an electronic identity corresponding to the second person to enable attaching at least the portion of the tracked physical activity of the first person to the electronic identity corresponding to the second person. In this manner, the proximity fitness tracking module 104 may be used for tracking physical activity of a person not wearing a physical activity tracking device (e.g., a person in close proximity to a person wearing a physical activity tracking device). In some embodiments, information other than physical activity of a second person in close proximity to a first person may be tracked by a device of the first person. For example, geospatial position, location, temperature, and so forth may be tracked by the first person and provided to an electronic identity of the second person that does not have a tracking device for the information tracked.

The data network 106, in one embodiment, includes a digital communication network that transmits digital communications. The data network 106 may include a wireless network, such as a wireless cellular network, a local wireless network, such as a Wi-Fi network, a Bluetooth® network, a near-field communication ("NFC") network, an ad hoc network, and/or the like. The data network 106 may include a WAN, a storage area network ("SAN"), a LAN, an optical fiber network, the internet, or other digital communication network. The data network 106 may include two or more networks. The data network 106 may include one or more servers, routers, switches, and/or other networking equipment. The data network 106 may also include computer readable storage media, such as a hard disk drive, an optical drive, non-volatile memory, RAM, or the like.

Figure 2:
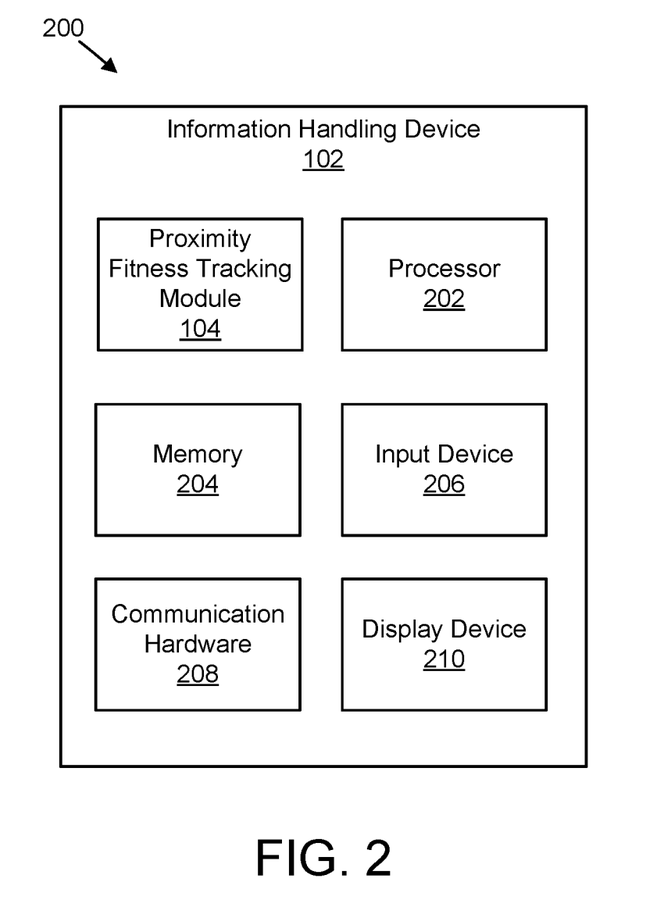
FIG. 2 is a schematic block diagram illustrating one embodiment of an apparatus including an information handling device.

FIG. 2 depicts one embodiment of an apparatus 200 that may be used for tracking physical activity. The apparatus 200 includes one embodiment of the information handling device 102. Furthermore, the information handling device 102 may include the proximity fitness tracking module 104, a processor 202, a memory 204, an input device 206, communication hardware 208, and a display device 210. In some embodiments, the input device 206 and the display device 210 are combined into a single device, such as a touchscreen.

The processor 202, in one embodiment, may include any known controller capable of executing computer-readable instructions and/or capable of performing logical operations. For example, the processor 202 may be a microcontroller, a microprocessor, a central processing unit ("CPU"), a graphics processing unit ("GPU"), an auxiliary processing unit, a field programmable gate array ("FPGA"), or similar programmable controller. In some embodiments, the processor 202 executes instructions stored in the memory 204 to perform the methods and routines described herein. The processor 202 is communicatively coupled to the memory 204, the proximity fitness tracking module 104, the input device 206, the communication hardware 208, and the display device 210.

The memory 204, in one embodiment, is a computer readable storage medium. In some embodiments, the memory 204 includes volatile computer storage media. For example, the memory 204 may include a RAM, including dynamic RAM ("DRAM"), synchronous dynamic RAM ("SDRAM"), and/or static RAM ("SRAM"). In some embodiments, the memory 204 includes non-volatile computer storage media. For example, the memory 204 may include a hard disk drive, a flash memory, or any other suitable non-volatile computer storage device. In some embodiments, the memory 204 includes both volatile and non-volatile computer storage media.

In some embodiments, the memory 204 stores data relating to tracking physical activity. In some embodiments, the memory 204 also stores program code and related data, such as an operating system or other controller algorithms operating on the information handling device 102.

The information handling device 102 may use the proximity fitness tracking module 104 for tracking physical activity. As may be appreciated, the proximity fitness tracking module 104 may include computer hardware, computer software, or a combination of both computer hardware and computer software. For example, the proximity fitness tracking module 104 may include circuitry, or a processor, used to detect, by use of the information handling device 102 held by a first person, a second person in close proximity to the first person. As another example, the proximity fitness tracking module 104 may include computer program code that tracks physical activity of the first person. As a further example, the proximity fitness tracking module 104 may include computer program code that transmits at least a portion of the tracked physical activity of the first person to an electronic identity corresponding to the second person to enable attaching at least the portion of the tracked physical activity of the first person to the electronic identity corresponding to the second person.

The input device 206, in one embodiment, may include any known computer input device including a touch panel, a button, a keyboard, a stylus, a microphone, an audio input, a sensor, or the like. In some embodiments, the input device 206 may be integrated with the display device 210, for example, as a touchscreen or similar touch-sensitive display. In some embodiments, the input device 206 includes a touchscreen such that text may be input using a virtual keyboard displayed on the touchscreen and/or by handwriting on the touchscreen. In some embodiments, the input device 206 includes two or more different devices, such as a keyboard and a touch panel. In various embodiments, the input device 206 may be used to detect a second person in close proximity to a first person. For example, the input device 206 may be used to detect a voice profile corresponding to the second person by using an audio input. As another example, the input device 206 may be used to detect an input indicating that the second person is in close proximity to the first person. The communication hardware 208 may facilitate communication with other devices. For example, the communication hardware 208 may enable communication via Bluetooth®, Wi-Fi, and so forth. In one embodiment, the communication hardware 208 may be used to detect a second person in close proximity to a first person. For example, in certain embodiments, the communication hardware 208 may detect a wireless device corresponding to the second person.

The display device 210, in one embodiment, may include any known electronically controllable display or display device. The display device 210 may be designed to output visual, audible, and/or haptic signals. In some embodiments, the display device 210 includes an electronic display capable of outputting visual data to a user. For example, the display device 210 may include, but is not limited to, an LCD display, an LED display, an OLED display, a projector, or similar display device capable of outputting images, text, or the like to a user. As another, non-limiting, example, the display device 210 may include a wearable display such as a smart watch, smart glasses, a heads-up display, or the like. Further, the display device 210 may be a component of a smart phone, a personal digital assistant, a television, a table computer, a notebook (laptop) computer, a personal computer, a vehicle dashboard, a streaming device, an activity tracking device, or the like.

In certain embodiments, the display device 210 includes one or more speakers for producing sound. For example, the display device 210 may produce an audible alert or notification (e.g., a beep or chime). In some embodiments, the display device 210 includes one or more haptic devices for producing vibrations, motion, or other haptic feedback. For example, the display device 210 may produce haptic feedback upon detecting a person in close proximity to the information handling device 102.

In some embodiments, all or portions of the display device 210 may be integrated with the input device 206. For example, the input device 206 and display device 210 may form a touchscreen or similar touch-sensitive display. In other embodiments, the display device 210 may be located near the input device 206. In certain embodiments, the display device 210 may receive instructions and/or data for output from the processor 202 and/or the proximity fitness tracking module 104.

Figure 3:
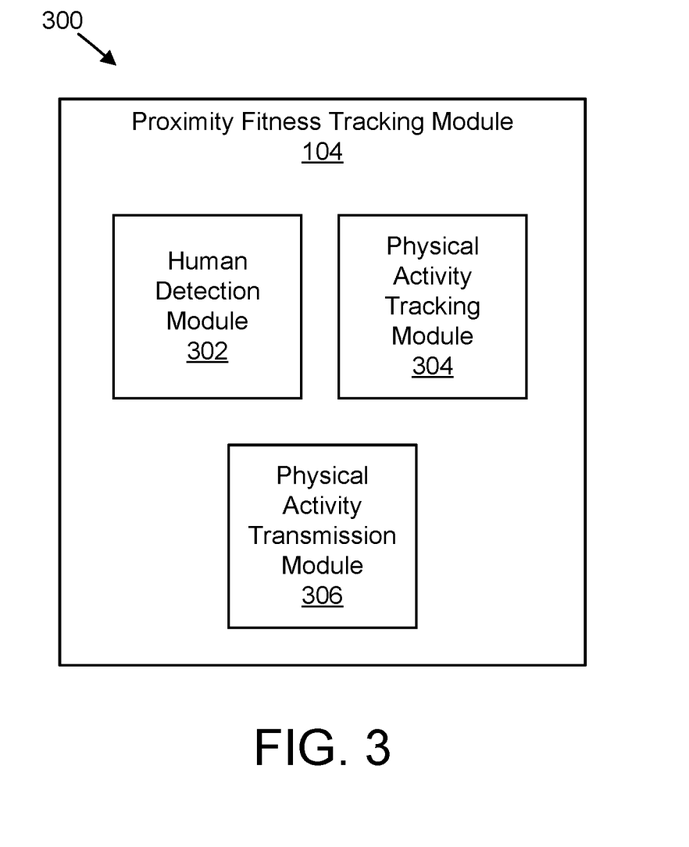
FIG. 3 is a schematic block diagram illustrating one embodiment of an apparatus including a proximity fitness tracking module.

FIG. 3 depicts a schematic block diagram illustrating one embodiment of an apparatus 300 that includes one embodiment of the proximity fitness tracking module 104. Furthermore, the proximity fitness tracking module 104 includes a human detection module 302, a physical activity tracking module 304, and a physical activity transmission module 306.

The human detection module 302 detects, by use of an apparatus held by a first person, a second person in close proximity to the first person. For example, the first person may have an apparatus (e.g., information handling device 102, such as a phone, fitness tracker, etc.) that dynamically detects that the second person is in close proximity to the first person (e.g., within 0-20 feet). As another example, the first person may have an apparatus that manually detects that the second person is in close proximity to the first person. As used herein, the term "held" may refer to holding in one's hand, having on one's person, having in a pocket, having in a purse, having in a bag, being attached to a person, being in something held by a person, having on an article of clothing, and so forth. Moreover, as used herein, a "second person" may refer to one or more people with the first person.

Figure 4:
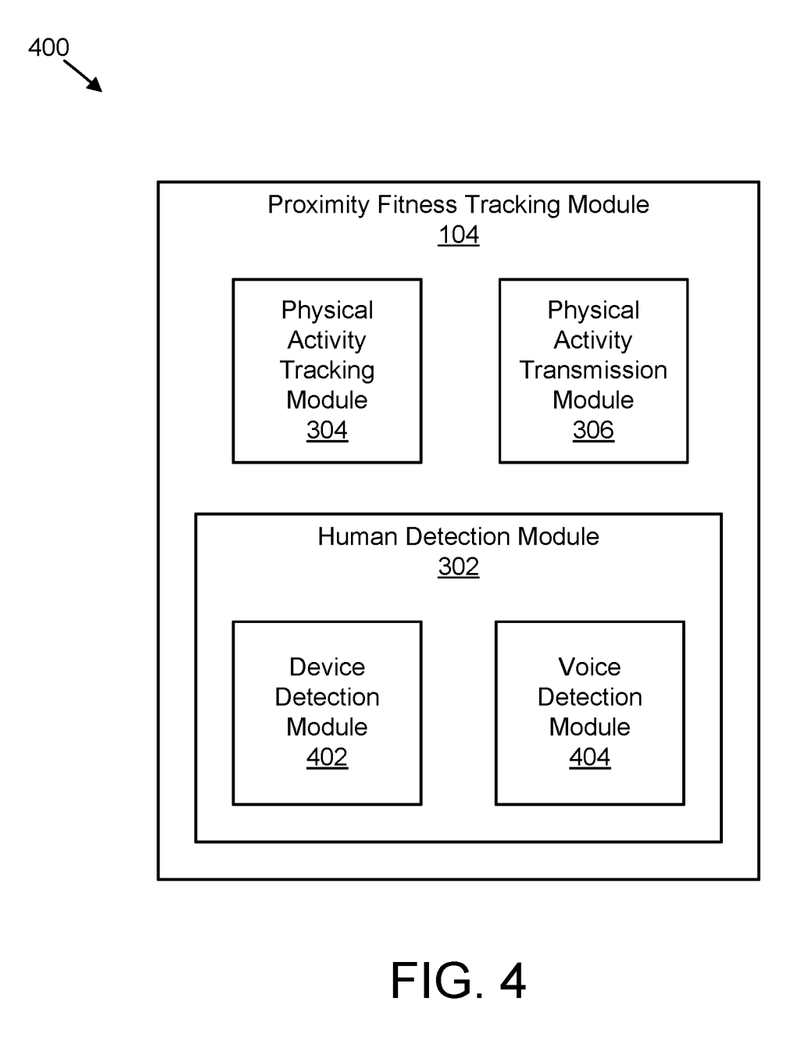
FIG. 4 is a schematic block diagram illustrating another embodiment of an apparatus including a proximity fitness tracking module.

In some embodiments, dynamically detecting that the second person is in close proximity to the first person may include detecting a wireless device corresponding to the second person and/or detecting a voice profile corresponding to the second person, as explained further in relation to FIG. 4. In various embodiments, manually detecting that the second person is in close proximity to the first person may include detecting an input to the human detection module 302 indicating that the second person is in close proximity to the first person. For example, the first person may input (e.g., via text, speech, video, picture, camera, etc.) to the human detection module 302 that the second person is with the first person. In one embodiment, the first person may type the second person's name to indicate that the second person is with the first person. In another embodiment, the first person may say the second person's name to indicate that the second person is with the first person. In a further embodiment, the first person may take a picture of the second person to indicate that the second person is with the first person. In another embodiment, the first person may take a video of the second person to indicate that the second person is with the first person. In any embodiment, the human detection module 302 may search contacts, friends, social media, electronic identities, email, messages, and so forth to identify the second person.

In certain embodiments, the human detection module 302 may obtain the electronic identity corresponding to the second person in response to detecting the second person. In certain embodiments, the human detection module 302 may search contacts, friends, social media, electronic identities, email, messages, and so forth to obtain the electronic identity of the second person. The electronic identity may be a name, a username, an identity, a login, a community name, an account name, an email address, and so forth associated with the second person for a particular website, such as a website used for tracking physical activity.

In one embodiment, the physical activity tracking module 304 tracks physical activity of the first person. For example, the physical activity tracking module 304 may track a number of steps the first person takes, a number of stairs a person steps, a location of the first person, a location of the first person over time, an elevation of the first person, an activity of the first person, and/or any movements corresponding to the first person.

In certain embodiments, the physical activity tracking module 304 may store information corresponding to time periods during the tracked physical activity in which the second person is detected to be in close proximity to the first person. For example, the human detection module 302 may provide an indication to the physical activity tracking module 304 that the second person is in close proximity to the first person, and the physical activity tracking module 304 may indicate with physical activity information that the first person and the second person are involved in the corresponding physical activity. As another example, the human detection module 302 may provide an indication to the physical activity tracking module 304 that the second person is no longer in close proximity to the first person, and the physical activity tracking module 304 may indicate with physical activity information that only the first person is involved in the corresponding physical activity.

In one embodiment, the physical activity of the first person may be tracked using the same apparatus that detects that the second person is in close proximity to the first person. In another embodiment, the physical activity of the first person may be tracked using a different apparatus (e.g., second apparatus) than the apparatus (e.g., first apparatus) that detects that the second person is in close proximity to the first person. In such an embodiment, the second apparatus may communicate with the first apparatus to determine when the second person is in close proximity to the first person. In some embodiments, detecting the second person in close proximity to the first person may occur in response to beginning tracking the physical activity of the first person using the physical activity tracking module 304.

The physical activity transmission module 306 transmits at least a portion of the tracked physical activity of the first person (e.g., the portion corresponding to the time that the second person was in close proximity to the first person) to an electronic identity corresponding to the second person to enable attaching at least the portion of the tracked physical activity of the first person to the electronic identity corresponding to the second person. Thus, the second person will be able to have information about their physical activity tracked and updated to their account using the physical activity tracking module 304 of the first person (e.g., without having their own physical activity tracking device).

FIG. 4 is a schematic block diagram illustrating another embodiment of an apparatus 400 that includes one embodiment of the proximity fitness tracking module 104. Furthermore, the proximity fitness tracking module 104 includes one embodiment of the human detection module 302, the physical activity tracking module 304, and the physical activity transmission module 306, that may be substantially similar to the human detection module 302, the physical activity tracking module 304, and the physical activity transmission module 306 described in relation to FIG. 3. The proximity fitness tracking module 104 also includes a device detection module 402 and a voice detection module 404.

The device detection module 402 detects that the second person is in close proximity to the first person by detecting a wireless device corresponding to the second person. For example, the second person may have an electronic device with them that is not capable of tracking physical activity. The device detection module 402 may detect the presence of the electronic device of the second person and may compare a digital identity of the electronic device to a stored digital identity. If the digital identity of the electronic device matches the stored digital identity corresponding to the second person, then the device detection module 402 will indicate that that the second person is in close proximity to the first person. The device detection module 402 may detect the wireless device corresponding to the second person using any suitable type of communication. For example, the device detection module 402 may use Wi-Fi, Bluetooth®, and so forth.

In some embodiments, the device detection module 402 may use a continuous low power scan to detect the wireless device corresponding to the second person. In various embodiments, the device detection module 402 may scan for previously paired devices to detect the wireless device corresponding to the second person. In certain embodiments, the device detection module 402 may detect the wireless device for a predetermined period of time before indicating that the wireless device is detected.

In some embodiments, the voice detection module 404 detects the second person in close proximity to the first person by detecting a voice profile corresponding to the second person (e.g., receiving voice data for the second person via an audio input, such as a microphone). In various embodiments, the voice detection module 404 detects the second person in close proximity to the first person by capturing audio input, comparing the audio input to stored voice profiles, and selecting the voice profile of the stored voice profiles that matches the audio input.

In certain embodiments, the voice detection module 404 may always listen (e.g., always on) to a microphone to detect a voice profile. In such embodiments, the voice detection module 404 may identify a non-owner voice pattern for a predetermined period of time before indicating that a voice profile has been detected. In some embodiments, voice profiles may be associated with contacts by the voice detection module 404 storing a voice profile for a person acquired during a phone call or other conversation with the person (e.g., actively listen to phone conversations and associate a detected voice with a contact in a contact list). In certain embodiments, voice profile information may be stored locally on an apparatus having the voice detection module 404. In various embodiments, voice profile information may be stored remotely from the apparatus (e.g., cloud storage). In some embodiments, the voice profile information may be accessible by multiple devices to enable the multiple devices to compare detected voice profiles to previously stored voice profiles.

Figure 5:
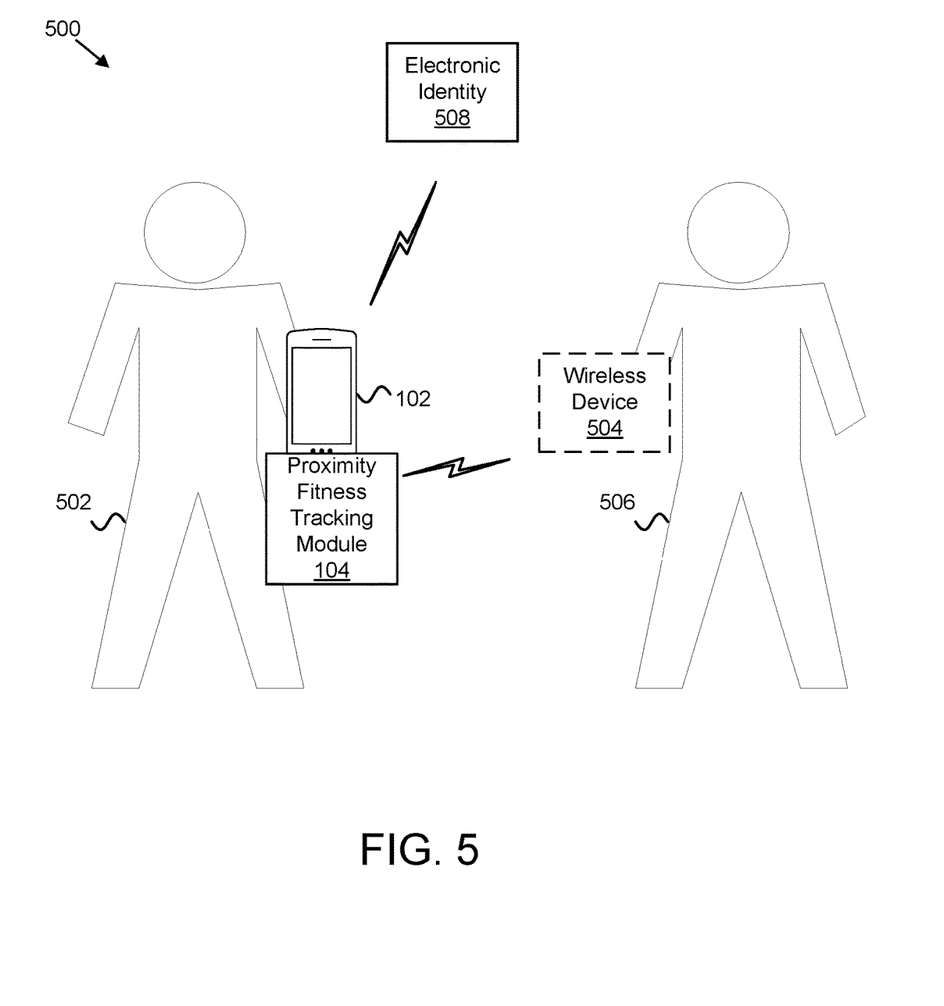
FIG. 5 is a diagram illustrating an embodiment of a system for tracking physical activity.

FIG. 5 is a diagram illustrating an embodiment of a system 500 for tracking physical activity. The system 500 illustrates a first person 502 having an information handling device 102 that includes the proximity fitness tracking module 104. The proximity fitness tracking module 104 may, in one embodiment, detect a wireless device 504 of a second person 506 to detect that the second person 506 is in close proximity to the first person 502. In certain embodiments, the proximity fitness tracking module 104 may detect a voice profile corresponding to the second person 504 to detect that the second person 506 is in close proximity to the first person 502. Moreover, the proximity fitness tracking module 104 may track physical activity of the first person 502 and may transmit at least a portion of the tracked physical activity of the first person 502 to an electronic identity 508 corresponding to the second person 506 to enable attaching at least the portion of the tracked physical activity of the first person 502 to the electronic identity 508 corresponding to the second person 506.

Figure 6:
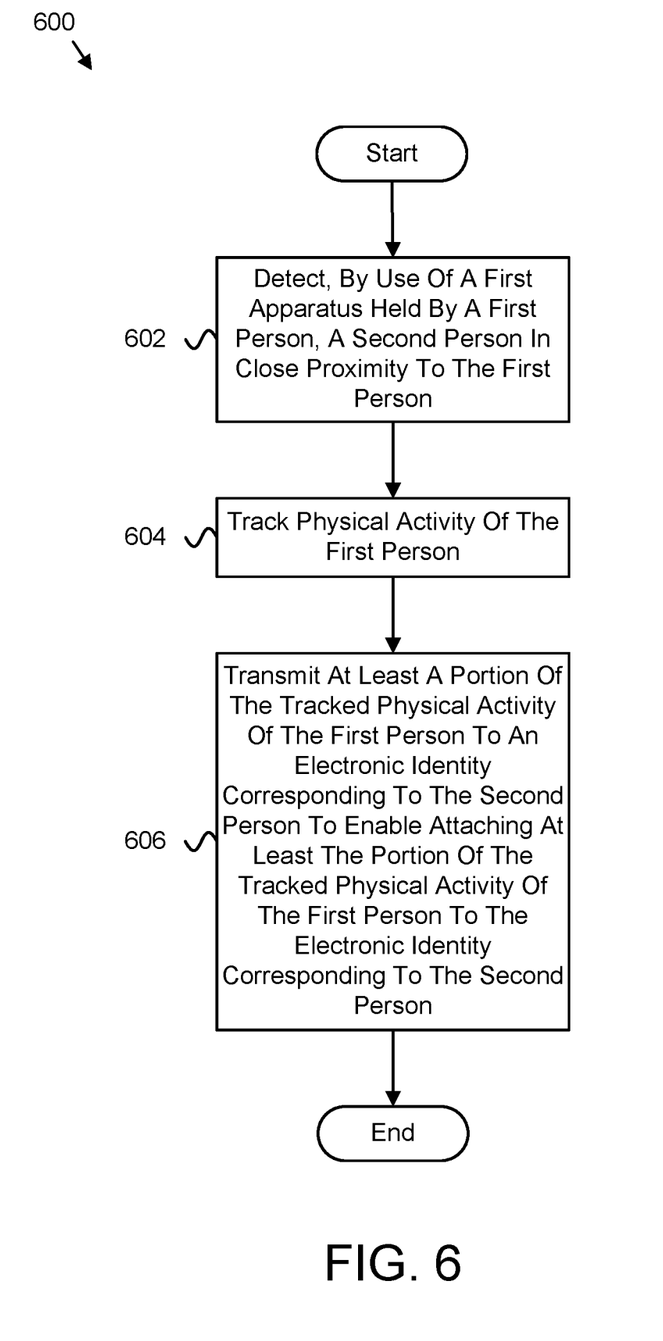
FIG. 6 is a schematic flow chart diagram illustrating an embodiment of a method for tracking physical activity.

FIG. 6 is a schematic flow chart diagram illustrating an embodiment of a method 600 for tracking physical activity. In some embodiments, the method 600 is performed by an apparatus, such as the information handling device 102. In other embodiments, the method 600 may be performed by a module, such as the proximity fitness tracking module 104. In certain embodiments, the method 600 may be performed by a processor executing program code, for example, a microcontroller, a microprocessor, a CPU, a GPU, an auxiliary processing unit, a FPGA, or the like.

The method 600 may include detecting 602, by use of a first apparatus held by a first person, a second person in close proximity to the first person. In certain embodiments, the human detection module 302 may detect 602 the second person in close proximity to the first person. In some embodiments, detecting 602 the second person in close proximity to the first person includes detecting a wireless device corresponding to the second person. In various embodiments, detecting 602 the second person in close proximity to the first person includes detecting a voice profile corresponding to the second person. In one embodiment, detecting the voice profile corresponding to the second person further includes: capturing audio input; comparing the audio input to multiple voice profiles; and selecting the voice profile of multiple voice profiles that matches the audio input. In certain embodiments, detecting 602 the second person in close proximity to the first person includes detecting an input to the first apparatus indicating that the second person is in close proximity to the first person. In various embodiments, detecting 602 the second person in close proximity to the first person comprises detecting the second person in response to beginning tracking the physical activity of the first person.

The method 600 may also include tracking 604 physical activity of the first person. In certain embodiments, the physical activity tracking module 304 may track 604 the physical activity of the first person. In some embodiments, tracking 604 the physical activity of the first person may include tracking the physical activity of the first person using the first apparatus, a second apparatus, or some combination thereof.

The method 600 may include transmitting 606 at least a portion of the tracked physical activity of the first person to an electronic identity corresponding to the second person to enable attaching at least the portion of the tracked physical activity of the first person to the electronic identity corresponding to the second person, and the method 600 may end.

In one embodiment, the method 600 may include storing information corresponding to time periods during the tracked physical activity in which the second person is detected to be in close proximity to the first person. In various embodiments, the method 600 includes obtaining the electronic identity corresponding to the second person in response to detecting the second person.

Figure 7:
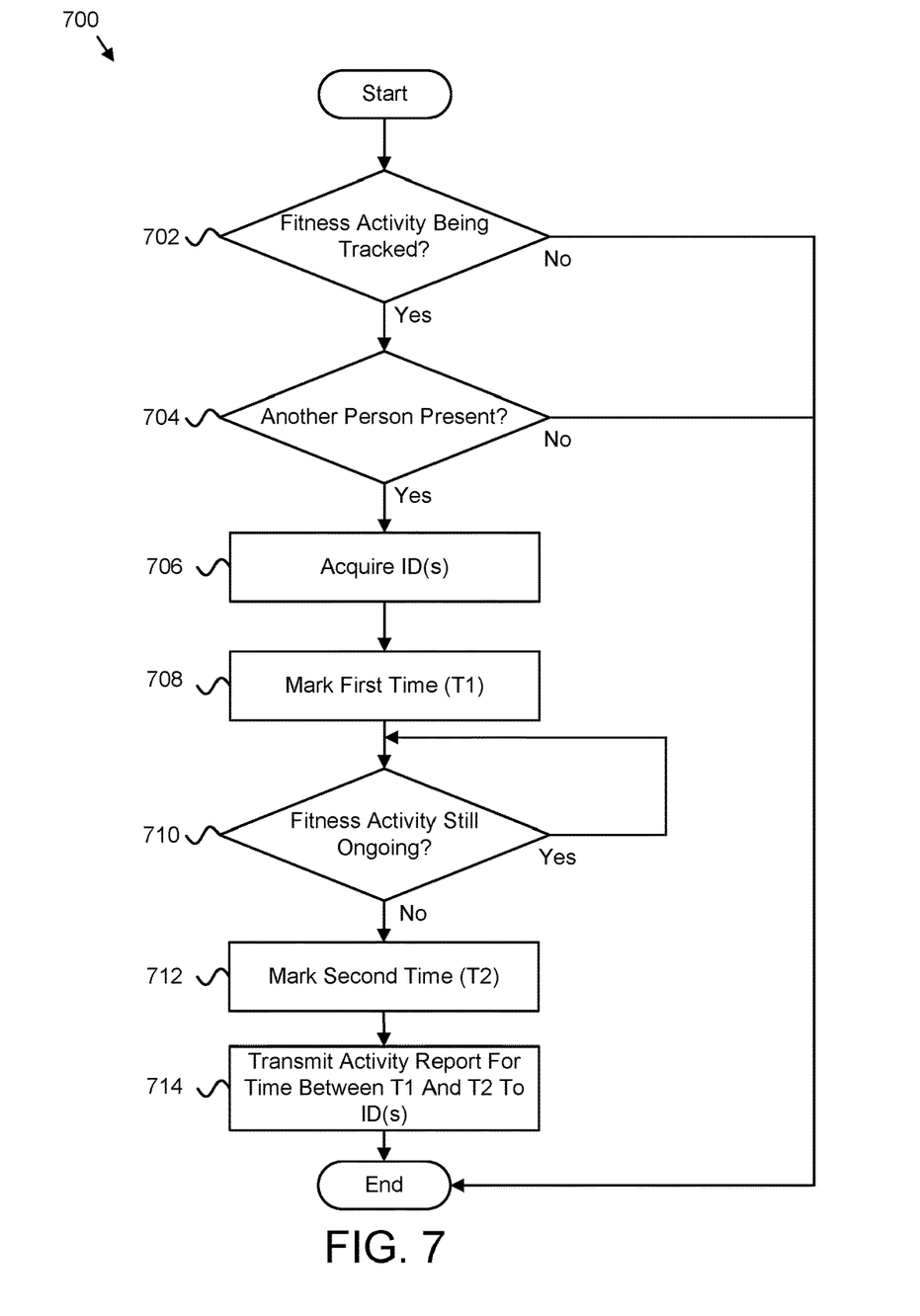
FIG. 7 is a schematic flow chart diagram illustrating another embodiment of a method for tracking physical activity.

FIG. 7 is a schematic flow chart diagram illustrating another embodiment of a method 700 for tracking physical activity. The method 700 includes determining 702 whether fitness activity (e.g., physical activity) is currently being tracked by a fitness tracking device of a first person. In response to fitness activity not being tracked, the method 700 may end.

In response to fitness activity being tracked, the method 700 includes determining 704 whether another person is present with the first person. In response to another person not being present with the first person, the method 700 may end. In response to another person (e.g., one or more people) being present with the first person, the method 700 may acquire 706 ID(s) (e.g., electronic identity(s)) corresponding to the one or more other people.

The method 700 may mark 708 a first time ("T1") indicating a time during which the first person is with one or more other people and fitness activity is being tracked. The method 700 determines 710 whether fitness activity is still ongoing and whether the first person is with the one or more other people. In response to fitness activity still ongoing and the first person still being with the one or more other people, the method 700 repeatedly determines 710 whether fitness activity is still ongoing and whether the first person is with the one or more other people. In response to fitness activity no longer ongoing or the first person no longer being with the one or more other people, the method 700 may mark 712 a second time ("T2") indicating a time during which the first person is either no longer with the one or more other people or fitness activity is no longer ongoing.

The method 700 may transmit 714 an activity report for the time between T1 and T2 to the ID(s) associated with the one or more other people so that the one or more other people may have a record of the fitness activity associated with their electronic identity(s).

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
    a processor;
    a memory that stores code executable by the processor to:
        detect, by use of the apparatus held by a first person, a second person in close proximity to the first person by detecting a wireless device corresponding to the second person, by detecting a voice profile corresponding to the second person, or a combination thereof;
        track physical activity of the first person, wherein the physical activity comprises a number of steps the first person takes, a number of stairs the first person steps, a location of the first person over time, an elevation of the first person, an activity of the first person, movements corresponding to the first person, or some combination thereof, and wherein the tracked physical activity comprises information indicating whether the second person is in close proximity to the first person at certain times during the physical activity upon detecting whether the second person is in close proximity to the first person during the physical activity; and
        transmit at least a portion of the tracked physical activity of the first person to an electronic identity corresponding to the second person as a result of detecting the second person in close proximity to the first person by detecting the wireless device corresponding to the second person, by detecting the voice profile corresponding to the second person, or the combination thereof to enable attaching at least the portion of the tracked physical activity of the first person to the electronic identity corresponding to the second person and to show that the second person had the same physical activity as the tracked physical activity of the first person, wherein the electronic identity corresponding to the second person comprises an account of the second person used to track physical activity of the second person, and the physical activity of the second person is stored on a storage device.

2. The apparatus of claim 1, wherein the code executable by the processor performs detecting the voice profile corresponding to the second person by comparing the voice profile to a plurality of voice profiles that are captured by the apparatus.

3. The apparatus of claim 2, wherein the code executable by the processor performs capturing the plurality of voice profiles by controlling the apparatus to actively listen to phone conversations and associating a detected voice with a contact in a contact list.

4. A method comprising:
    detecting, by use of a first apparatus held by a first person, a second person in close proximity to the first person by detecting a wireless device corresponding to the second person, by detecting a voice profile corresponding to the second person, or a combination thereof;
    tracking physical activity of the first person, wherein the physical activity comprises a number of steps the first person takes, a number of stairs the first person steps, a location of the first person over time, an elevation of the first person, an activity of the first person, movements corresponding to the first person, or some combination thereof, and wherein the tracked physical activity comprises information indicating whether the second person is in close proximity to the first person at certain times during the physical activity upon detecting whether the second person is in close proximity to the first person during the physical activity; and
    transmitting at least a portion of the tracked physical activity of the first person to an electronic identity corresponding to the second person as a result of detecting the second person in close proximity to the first person by detecting the wireless device corresponding to the second person, by detecting the voice profile corresponding to the second person, or the combination thereof to enable attaching at least the portion of the tracked physical activity of the first person to the electronic identity corresponding to the second person and to show that the second person had the same physical activity as the tracked physical activity of the first person, wherein the electronic identity corresponding to the second person comprises an account of the second person used to track physical activity of the second person, and the physical activity of the second person is stored on a storage device.

5. The method of claim 4, wherein detecting the voice profile corresponding to the second person further comprises:
    capturing audio input;
    comparing the audio input to a plurality of voice profiles; and
    selecting the voice profile of the plurality of voice profiles that matches the audio input.

6. The method of claim 4, further comprising storing information corresponding to time periods during the tracked physical activity in which the second person is detected to be in close proximity to the first person.

7. The method of claim 4, wherein tracking the physical activity of the first person comprises tracking the physical activity of the first person using the first apparatus, a second apparatus, or some combination thereof.

8. The method of claim 4, wherein detecting the second person in close proximity to the first person comprises detecting the second person in response to beginning tracking the physical activity of the first person.

9. The method of claim 4, further comprising obtaining the electronic identity corresponding to the second person in response to detecting the second person.

10. A program product comprising a non-transitory computer readable storage medium that stores code executable by a processor, the executable code comprising code to perform:
  detecting, by use of a first apparatus held by a first person, a second person in close proximity to the first person by detecting a wireless device corresponding to the second person, by detecting a voice profile corresponding to the second person, or a combination thereof;
  tracking physical activity of the first person, wherein the physical activity comprises a number of steps the first person takes, a number of stairs the first person steps, a location of the first person over time, an elevation of the first person, an activity of the first person, movements corresponding to the first person, or some combination thereof, and wherein the tracked physical activity comprises information indicating whether the second person is in close proximity to the first person at certain times during the physical activity upon detecting whether the second person is in close proximity to the first person during the physical activity; and
  transmitting at least a portion of the tracked physical activity of the first person to an electronic identity corresponding to the second person as a result of detecting the second person in close proximity to the first person by detecting the wireless device corresponding to the second person, by detecting the voice profile corresponding to the second person, or the combination thereof to enable attaching at least the portion of the tracked physical activity of the first person to the electronic identity corresponding to the second person and to show that the second person had the same physical activity as the tracked physical activity of the first person, wherein the electronic identity corresponding to the second person comprises an account of the second person used to track physical activity of the second person, and the physical activity of the second person is stored on a storage device.

11. The program product of claim 10, wherein the executable code further comprises code to perform storing information corresponding to time periods during the tracked physical activity in which the second person is detected to be in close proximity to the first person.

12. The program product of claim 10, wherein tracking the physical activity of the first person comprises tracking the physical activity of the first person using the first apparatus, a second apparatus, or some combination thereof.

13. The program product of claim 10, wherein the executable code further comprises code to perform obtaining the electronic identity corresponding to the second person in response to detecting the second person.

14. The program product of claim 10, wherein the executable code further comprises code to perform detecting a voice profile corresponding to the second person.

15. The program product of claim 14, wherein the executable code to perform detecting the voice profile corresponding to the second person further comprises code to perform:
  capturing audio input;
  comparing the audio input to a plurality of voice profiles; and
  selecting the voice profile of the plurality of voice profiles that matches the audio input.

* * * * *